(12) United States Patent
Hellstrom

(10) Patent No.: US 6,588,118 B2
(45) Date of Patent: Jul. 8, 2003

(54) NON-CONTACT SHEET SENSING SYSTEM AND RELATED METHOD

(75) Inventor: Ake Arvid Hellstrom, Columbus, OH (US)

(73) Assignee: ABB Inc., Norwalk, CT (US)

( * ) Notice: Subject to any disclaimer, the term of this patent is extended or adjusted under 35 U.S.C. 154(b) by 0 days.

(21) Appl. No.: 09/974,358

(22) Filed: Oct. 10, 2001

(65) Prior Publication Data

US 2003/0066200 A1 Apr. 10, 2003

(51) Int. Cl.⁷ .................................................. G01B 7/06
(52) U.S. Cl. ................ 33/501.02; 33/501.03; 33/DIG. 1; 33/DIG. 2
(58) Field of Search .......................... 33/501.02, 501.03, 33/501.04, 783, DIG. 1, DIG. 2

(56) References Cited

U.S. PATENT DOCUMENTS

| | | | |
|---|---|---|---|
| 3,528,002 A | * 9/1970 | Dunlavey | 33/501.03 |
| 3,818,327 A | * 6/1974 | Alexander | 33/501.03 |
| 3,855,524 A | 12/1974 | Crawford | |
| 4,292,838 A | 10/1981 | Larsen | |
| 4,434,649 A | 3/1984 | Williams | |
| 4,449,398 A | 5/1984 | Williams | |
| 4,450,404 A | 5/1984 | Williams et al. | |
| 4,791,367 A | 12/1988 | Typpo | |
| 4,877,485 A | 10/1989 | Carson | |
| 4,901,445 A | 2/1990 | Boissevain et al. | |
| 4,929,895 A | 5/1990 | Typpo | |
| 5,042,160 A | 8/1991 | Kasten et al. | |
| 5,111,592 A | 5/1992 | Aehnelt et al. | |
| 5,132,619 A | 7/1992 | Typpo | |
| 5,226,239 A | 7/1993 | Boissevain et al. | |
| 5,243,849 A | 9/1993 | Williams | |
| 5,297,062 A | 3/1994 | Cresson et al. | |
| 5,355,589 A | 10/1994 | Madlener et al. | |
| 5,479,720 A | 1/1996 | Hellstrom et al. | |

OTHER PUBLICATIONS

General Specifications (Models BM8BC1/BM8BC2) Caliper Sensor; 1993; GS 14H6H0–01E; Yokogawa; Tokyo.
On line DickenmeBsysteme Typ DM–LL DM–LV DM–SH; Paul Lippke GmbH & Co. KG; Germany.
The Advantage Line Process Management System, Model 4406 Caliper Sensor, Model 4407 Caliper/RF Moisture Sensor; Impact Systems; San Jose, California.
The Advantage Line Process Management System, Model 4410 LT (Light Touch) Caliper Sensor; 1991; 618 SCOP/5–91/2K; Impact Systems; San Jose, California.
RS (Rapid–Scanning) Caliper Measurement Models 4203/4163/4168; Impact Systems; San Jose, California.

* cited by examiner

Primary Examiner—Christopher W. Fulton
(74) Attorney, Agent, or Firm—Stevens & Showalter LLP

(57) ABSTRACT

A non-contact system for sensing a property of a passing web of material includes first and second sensors positioned on opposite sides of the web. The opposing sensors are repelled from the web and each other by gas bearings formed between the sensors and the web and attracted to each other by one or more polarized magnets embedded in the sensors. The resultant net force properly spaces the sensors from the web to ensure reliable and accurate sensing. The repelling force enables the sensors to react substantially instantaneously to changes in the pass line of the web. An automatic actuator/retractor can be provided to withdraw the sensors, extend the sensors to or retract the sensors from adjacent the feed path.

24 Claims, 9 Drawing Sheets

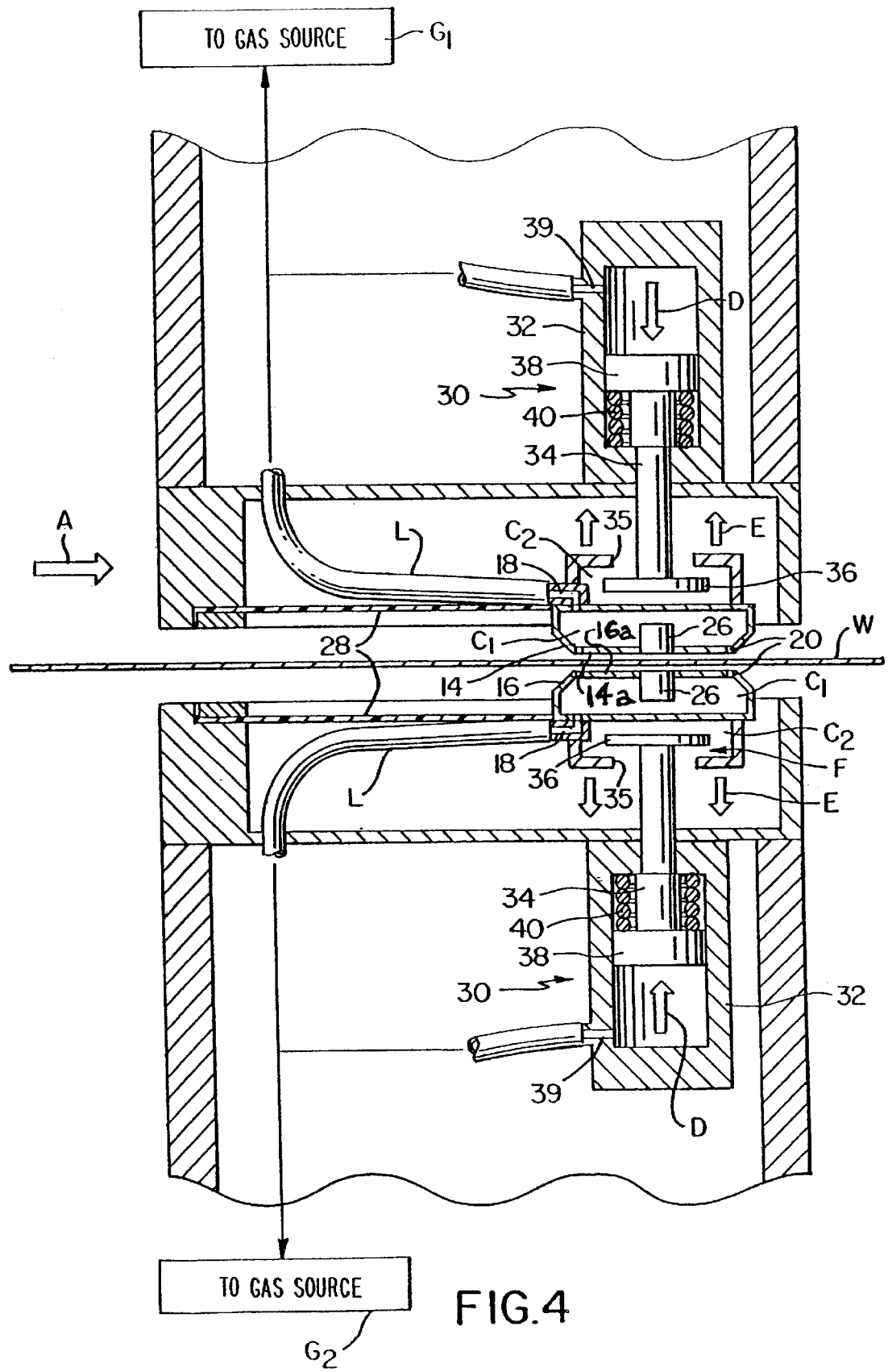

NON-CONTACT SHEET SENSING SYSTEM AND RELATED METHOD

TECHNICAL FIELD

The present invention relates generally to sensors for use with moving sheets or webs of material and, more particularly, to a non-contact sensor system for measuring or sensing properties or characteristics of a substantially continuous sheet or web of paper.

BACKGROUND OF THE INVENTION

Systems for measuring characteristics or properties of moving sheets or webs of material are well known in the art. Typically, these systems employ first and second sensors in the form of sensing heads or shoes positioned on the opposite sides of a passing web. These sensors contain sensitive electronic, radiation or optical detection systems for measuring one or more characteristics of the passing web, such as thickness, opacity, moisture, gloss, smoothness, or other properties. Commonly, the moving web travels in a free gap between two scanning sensor heads and sheet properties are measured via an arrangement with sensing devices in upper and lower heads. In order to measure certain sheet properties, including but not restricted to thickness (also known as caliper), gloss or smoothness, a controlled and close proximity of the sensing heads to the sheet surface is advantageous in order to achieve acceptable accuracy. This can be partially accomplished by pass line control from sheet guide devices attached to the sensor heads, or preferably by using flexible mounts for the system that permit relative sensor movement in at least the vertical plane. An example of such a system and, in particular, one type of sensing head for contacting and measuring characteristics of a passing web of paper, is shown and described in commonly assigned U.S. Pat. No. 5,479,720 to Hellstrom et al., the disclosure of which is incorporated herein by reference.

In order to ensure that the selected characteristics or properties of the web are accurately measured, it often is desirable to position the opposed first and second sensors as close as possible to the web without contacting the web. Also, the first and second sensors must be in close alignment with one another in the web plane to ensure that any measurements taken correspond to substantially the same area of the passing web. This alignment requires careful manual adjustment of the sensing heads as well as costly precision scanning mechanisms, but can still never be fully attained. Simultaneously meeting both requirements is complicated by the fact that the pass line of the web relative to the sensors may rapidly change as a result of events occurring upstream or downstream of the system. Accordingly, not only must the mounting arrangement be capable of securely and reliably holding the sensors in a precisely controlled, spaced, and aligned relationship adjacent to the corresponding side of the web, but it must also be capable of rapidly responding to changes in the pass line. Also, contact or engagement between the sensors must be avoided to prevent the instrumentation held therein from damage, especially when the web of passing material is absent from the feed path.

In the '720 patent, the sensors are designed to make actual physical contact with the passing web. This is possible due to specialized low-friction, wear-resistant contact surfaces formed of ceramic materials. A flexible mounting also ensures that the sensors are not only kept aligned in the web plane, but may also move as necessary in the vertical plane to ensure that the sensing heads can accommodate any rapid changes in the pass line of the web. Despite the advances offered by this solution, each sensor still directly contacts the web of passing material during sensing, which is not the most desirable for sensing or detecting properties of characteristics of certain web materials due to possible disruption or damage of the web at the location of contact.

One method to avoid web contact is to deploy a large free gap between upper and lower heads. This eliminates any sheet contact but typically reduces sensor accuracy since the sheet can flutter anywhere between heads and the sheet may not be flat, or parallel with the gap. Prior art suggests remedies with pass line control devices including rollers, air guides and vacuum plates to hold the moving sheet at a controlled position. This is difficult to accomplish on a fast moving or non-flat sheet and it solves only part of the problem. Examples of devices for sheet pass line control are disclosed in U.S. Pat. Nos. 4,877,485 (Carson); 4,449,398 (Williams); and, 5,654,799 (Chase). These methods have the common disadvantage of controlling the pass line to only one of either the upper or lower heads since the pass line cannot be controlled to both heads simultaneously due to variable head alignment.

In order to achieve non contacting thickness measurement in close proximity with the sheet, others have proposed supplying pressurized air to form a gas bearing between a single sensor or a pair of opposing sensors on one or both sides of a passing web. Usually, the air bearing sensors are supported by fixed or flexible mountings. These mountings create a measurement force against the process in order to balance the repelling force created by the air bearing(s) from moving the sensors to permit accurate measurements. However, in such a passive arrangement, the measurement force must be carefully controlled to ensure that the sensor (s) remain even approximately spaced at the desired distance from the web at all times, or a complex pneumatic or mechanical system is required. Furthermore, since the sheet may have curl, waves and draw wrinkles, it is not possible to apply a sensing force that is always at a normal to the sheet plane in such arrangements. Where two opposed sensors are provided, creating the desired spacing using air bearings with fully articulated mountings would require complex designs.

Non-contacting measurement of sheet thickness using a magnetic measurement system separated by air bearings on one or both sides of the process is known in prior art, for instance as disclosed in U.S. Pat. Nos. 5,243,849 (Williams); 4,528,507 (Williams et al.); 4,647,855 (Berglund); 5,865,059 (Alessandro); 4,292,838 (Larsen); and, 4,107,606 (Typpo). Although these designs eliminate sheet contact on one or both sides of the sheet, the accuracy of sensors using these methods has not been acceptable due to excessive web influence parameters including web flutter, waves and smoothness changes as well as measurement errors caused by head misalignment.

Other non-contacting thickness measurement methods have been suggested including distance measurement across a pair of large free gap sensing heads that measure location of the upper and lower paper surface relative to each sensor head augmented with gap measurement devices for measuring the head to head separation. Examples of methods for optical thickness measurement using this arrangement are disclosed in U.S. Pat. Nos. 5,210,593 (Kramer); 5,805,291 (Calvin, et al.); 5,355,083 (George, et al.); 4,358,960 (Porter); 6,281,679 (King) and, WO00/37885 (King, et al.). An example of ultrasonic thickness measurement using this arrangement is disclosed in U.S. Pat. No. 5,113,358 (Reber). The prior art involves sheet surface location sensing devices spaced by a certain large distance from the sheet, to maintain a safe separation for no contact with the process, in conjunction with magnetic gap measurement. The large separation distance presents a challenge to measure a large dimension accurately in order to estimate a sheet thickness value that is much smaller than this distance. Product quality requirements for fabrication of many paper products demand measurement errors no larger than one half micron (0.5× $10^{-6}$ meter) at any point across the web. This has to be fulfilled despite severe environmental conditions, a scanning device with certain mechanical errors between upper and lower heads, plus a process with variable pass line, curl and sheet surface conditions. Thus, in principle, these methods produce a non-contacting thickness measurement; but in practice, they never have achieved acceptable measurement accuracy in typical paper industry applications.

On-line measurement of optical surface properties, like gloss or smoothness, on one or both sides of paper webs can have measurement errors introduced by sheet flutter, non-flat sheets, sensor head deflections or vibrations. Examples of prior art gloss measurement are disclosed in U.S. Pat. Nos. 6,233,053 (Preston); 6,031,620 (Typpo); and 4,830,504 (Frohardt). An example of prior art on-line smoothness measurement is disclosed in U.S. Pat. No. 5,654,799 (Chase, et al.). The main unresolved problem in this prior art is the inability to simultaneously control a moving web relative to measurement heads on each side of the web, since each head is subject to deflection errors and sheet flutter. Another problem is introduced by the large free gap necessary for a safe non-contacting web passage. These problems makes it difficult to construct a physically small sensor with a narrow measurement area, since there is a general scaling rule that dictates the size of the optical system in relation to the maximum free distance to the web. Such constraints have limited the accuracy and practicality of on-line measurement of gloss and smoothness as well as additional sheet properties including formation, brightness, opacity, color, basis weight and moisture.

Accordingly, a need exists for a web material property sensing platform in which opposed first and second non-contact sensors remain aligned in the web plane and evenly spaced in close proximity to a web of passing material at all times, even when the pass line or sheet curl changes rapidly, and a method for achieving accurate measurement of thickness, optical and other sheet properties by means of integrating magnetic, optical or other sensing elements in this platform with a close proximity to, but not contacting, the process surface.

SUMMARY OF THE INVENTION

This need is met by the invention of the present application wherein a non-contact, sheet sensing system employs first and second sensors positioned on opposite sides of a passing web with the sensors being simultaneously repelled from the passing web and attracted to each other. The resultant net force keeps the sensors closely and evenly spaced from the passing web to ensure that reliable and precise sensing or detecting functions are provided. Since the sensors are repelled from the web, they react substantially instantaneously to any changes in the pass line or curling of the web as it moves along the feed path while the attractive force keeps any relative tilting or movement of the sensors in check. In one embodiment of the invention, an automatic actuator/retractor retracts the sensors to ensure that the sensors do not contact each other when the web is absent from the feed path, and may also be used to withdraw the sensors from adjacent the web as necessary. The sensing system results in a great improvement over prior art efforts to provide non-contact sensors for a passing sheet or web of material, especially in terms of operational reliability and accuracy.

Thus, the sensors of the present application enable non-contact sensing of surface properties on one or both sides of the web, as well as reflective/transmissive properties of the web by sensing elements located within the sensors in close and controlled proximity to the web surfaces. Web properties that can be measured by sensing elements in the sensors may include, but are not restricted to, caliper, surface smoothness, gloss, brightness, opacity and formation.

In accordance with a first aspect of the present invention, a non-contact system for sensing or measuring a property or characteristic of a sheet or web of material moving along a feed path comprises a first sensor positioned adjacent a first side of the feed path. The first sensor includes a passage for receiving pressurized gas and directing the gas toward the web when it is present in the feed path. A second sensor is positioned adjacent a second side of the feed path opposing the first sensor. The second sensor also includes a passage for receiving pressurized gas and directing the gas toward the web in the feed path. At least one magnet is mounted in each of the first and second sensors, with the magnet of the first sensor being aligned with and attracted to the magnet of the second sensor and forming a magnetic coupling. This magnetic coupling urges the sensors toward the corresponding side of the web and one another, with the gas directed toward the web from the first and second sensors forming gas bearings that simultaneously urge the sensors away from the web. As a result, a net force generated by the magnets and the gas bearings keeps the sensors substantially evenly spaced from the web passing along the feed path, thereby ensuring accurate sensing and measuring of the desired properties or characteristics of the web.

To permit relative movement of the sensors in the vertical plane, a first flexible mount is provided for the first sensor and a second flexible mount is provided for the second sensor. This relative movement capability ensures that the first and second sensors may remain substantially parallel to the passing web of material at all times, even during changes in the pass line and the process itself. At least one of the first and second flexible mounts may also permit movement of the associated sensor in the horizontal plane. However, as should be appreciated, the associated sensor is prevented from moving any significant distance in this plane relative to the other sensor when the first and second sensors are magnetically coupled to one another.

The magnet of the first sensor may comprise a first plurality of magnets that align with and correspond to a second plurality of magnets comprising the magnet in the second sensor, with north and south poles facing each other to create an attraction force.

The sensing system may also include an actuator associated with at least one of the first and second sensors. In operation, each actuator enables or urges the associated sensor to move toward the feed path and the opposite sensor. Preferably, first and second actuators are associated with the first and second sensors, respectively, with the first and second actuators together enabling or urging the first and second sensors to move toward one another.

In one possible embodiment, each actuator comprises a pneumatic cylinder including a plunger having a first head for engaging the corresponding sensor. When each of the cylinders is pressurized, the corresponding plunger moves the sensor associated therewith toward the feed path and the opposite sensor. Each plunger further includes a second head disposed in the pneumatic cylinder for engaging a spring held therein. Upon de-pressurizing the pneumatic cylinders, the springs bias the corresponding plungers away from the web and thereby retract the corresponding sensors. Thus, each sensor "floats" on the first head of the corresponding plunger upon actuation as a result of the net force created by the combination of the attractive force supplied by the magnetic coupling and the repelling force created by the gas bearings, as well as the flexible mountings that permit the sensors to move up and down in the vertical plane and to tilt. Preferably, each pneumatic cylinder is in communication with and activated by the pressurized gas also used to form the gas bearings. Accordingly, the first and second sensors are automatically retracted upon a loss of pressure in the pressurized gas.

In accordance with a second aspect of the present invention, a non-contact system for sensing or measuring a property or characteristic of a web of material moving along a feed path is provided. The system comprises first and second sensors positioned on opposite sides of the feed path. Each of the first and second sensors includes at least one magnet, an inlet for receiving a pressurized gas, and at least one outlet for directing pressurized gas toward the feed path to create first and second gas bearings for the web of material when present. The at least one magnet of the first sensor is aligned with and attracted to the at least one magnet of the second sensor by magnetic coupling, which in turn aligns and urges the first and second sensors toward one another and the web. However, the gas directed from each of the first and second sensors to form the first and second gas bearings simultaneously urges the sensors away from the web and one another so that the net force keeps the sensors closely and substantially evenly spaced from the web moving along the feed path.

In one embodiment, the sensor system also comprises a first retractor for engaging and moving a first sensor away from a second sensor and the feed path defined between the first and second sensors, and a second retractor for engaging and moving the second sensor away from the first sensor and the feed path. Each of the first and second retractors comprises a cylinder including a pressure-activated plunger having a first head for engaging the corresponding sensor and a second head disposed in the cylinder for engaging a spring held therein. Thus, upon relieving the pressure in each cylinder, the spring biases the second head of the plunger such that the first head engages and moves the corresponding sensor away from the feed path. Preferably, the cylinders of the first and second retractors comprise pneumatic cylinders, but the use of other equivalent arrangements is of course possible.

In accordance with a third aspect of the present invention, first and second sensors are provided for use in an overall system for measuring or sensing a property or characteristic of a web of material moving along a feed path. Each sensor comprises a sensor head including at least one magnet, an inlet for receiving pressurized gas, and at least one outlet for issuing the pressurized gas towards a passing web of material to form a gas bearing. The first and second opposed sensors are simultaneously attracted and aligned by the magnets and repelled by the gas bearings to keep the first and second opposed sensors evenly spaced from the passing web.

In accordance with a fourth aspect of the present invention, a method of sensing or measuring a property or characteristic of a web of material moving along a feed path is provided. The method comprises positioning first and second opposed sensors adjacent to and on opposite sides of the feed path. Each of the sensors includes a magnet. Together, these magnets form a magnetic coupling that serves to align and draw the sensors toward one another and the web of material passing through the feed path. The method also includes the step of pressurizing passages in the sensors to form a fluid bearing on either side of the web so that net magnetic and bearing forces keep the sensors closely and substantially evenly spaced from the passing web. The method may also include the step of retracting the sensors when the web of material is not to be sensed.

In accordance with a fifth aspect of the present invention, a method of sensing or measuring a property or characteristic of a web of material moving along a feed path comprises positioning a first sensor on one side of a web of material in the feed path and positioning a second sensor on a second side of the web of material. The first and second sensors are drawn toward one another and the web of material with a magnetizing force, and repelled from one another and the web with a repelling force. The magnetizing force and repelling force are controlled to maintain the first and second sensors closely and evenly spaced from the passing web.

In one embodiment, repelling the first and second sensors from one another and the web comprises forming gas bearings in the first and second sensors and applying pressurized gas to the gas bearings. Also, drawing the first and second sensors toward one another and the web of material comprises mounting at least one magnet on the first sensor and mounting at least one magnet on the second sensor, wherein the magnet on the first sensor and the magnet on the second sensor are polarized to attract one another. Preferably, the first and second sensors have a substantially flat surface facing the feed path, and the at least one magnet of the first sensor is recessed below the substantially flat surface of the first sensor, while the at least one magnet of the second sensor is recessed below the substantially flat surface of the second sensor.

BRIEF DESCRIPTION OF THE DRAWINGS

FIG. 2b is a partially sectioned schematic front view of the opposing pair of sensors of the alternate embodiment shown in FIG. 2a;

FIG. 4 is a view similar to FIG. 3 but showing the sensors moved into sensing position adjacent the web by the actuators/retractors;

FIG. 5b is a partially sectioned frontal view of the opposing pair of sensors of the alternate embodiment shown in FIG. 5a;

FIG. 6b is a partially sectioned front view of the opposing pair of sensors of the alternate embodiment shown in FIG. 6a;

FIG. 7b is a partially sectioned front view of the opposing pair of sensors of the alternate embodiment shown in FIG. 7a.

DETAILED DESCRIPTION OF THE INVENTION

Figure 1A:
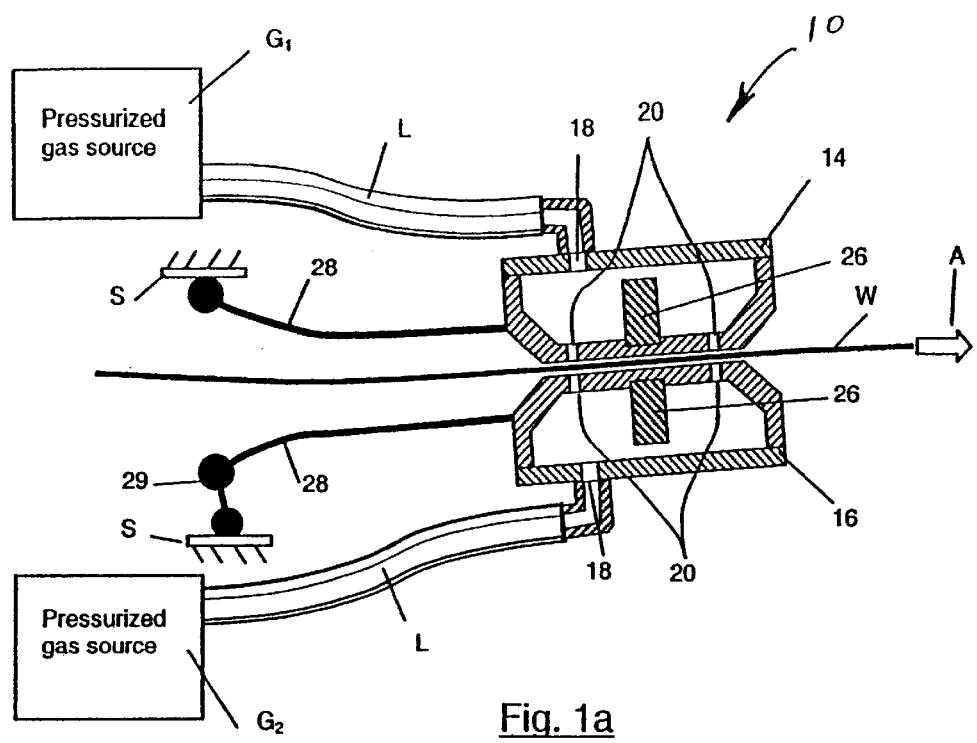
FIG. 1a is a partially sectioned schematic side view of one possible embodiment of the sensing system of the present invention.

Reference is now made to FIG. 1a, which illustrates one possible embodiment of the sensing system 10 of the present invention. The system 10 includes first and second sensors 14, 16 in the form of sensor heads or shoes. The first and second sensors 14, 16 are positioned in an opposing relationship along a feed path of a moving sheet or web of material, such as a web of paper W or the like. As described in commonly assigned U.S. Pat. No. 5,479,720, the sensors 14, 16 usually are mounted on transverse beams of a scanner (not shown) and are driven to and fro across the width of the passing web W in substantial alignment with each other in the horizontal plane. As is well known in the art, the web of paper W is initially formed in an upstream portion of a paper making machine (not shown) and progresses to downstream processing equipment including calendaring rolls and the like for further processing. The direction of web travel is shown by arrow A in FIG. 1a.

Figure 1B:
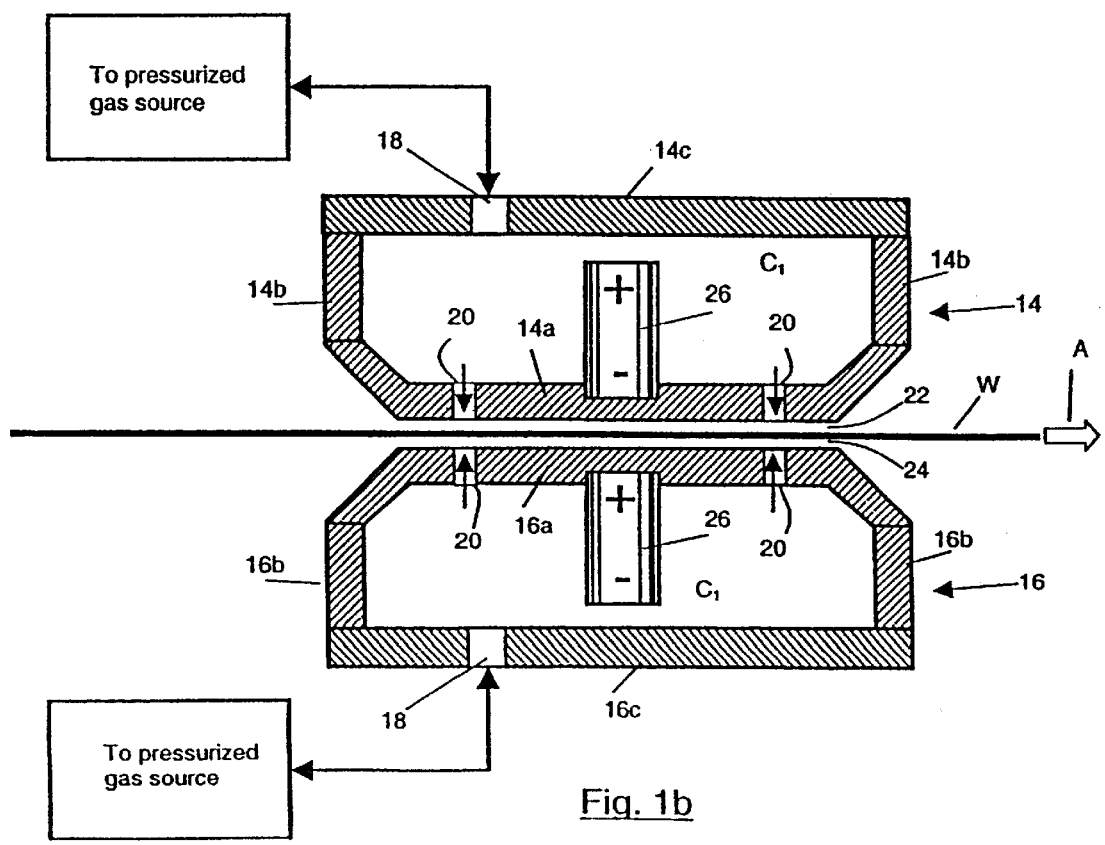
FIG. 1b is a partially sectioned schematic side view of the opposing sensors of the system of FIG. 1a on an enlarged scale.

In this embodiment, each of the first and second sensors 14, 16 comprises a cylindrical body or housing including a substantially flat face 14a, 16a for facing the web W, an annular sidewall 14b, 16b, and a connecting wall 14c, 16c opposing the face (see FIG. 1b). Together, these walls define a first chamber $C_1$ for, among other things, housing the instrumentation (not shown) used to detect or sense desired properties or characteristics of the web W, such as for example, magnetic sensors or optical sensors.

The housing for each of the first and second sensors 14, 16 also includes a passage 18 for receiving pressurized gas, such as air, and introducing the pressurized gas into the chamber $C_1$. Preferably, the passage 18 is formed in the connecting wall 14c, 16c of the first and second sensors 14, 16. The pressurized gas for the first and second sensors 14, 16 may be supplied by separate gas sources $G_1$, $G_2$, as illustrated schematically in FIG. 1a, or by a single source (see FIG. 3). The pressurized gas is conveyed by a tube that can be any appropriate form of gas conduit or line L that is sufficiently flexible so that it does not interfere with the relative movement of the corresponding sensors 14, 16.

At least one outlet is formed in the substantially flat face 14a, 16a of each of the first and second sensors 14, 16, with a plurality of outlets 20 being formed in the illustrated embodiments. The plurality of outlets 20 in each of the sensors 14, 16 are arranged in a circular pattern in the embodiment illustrated in FIG. 2a. The outlets 20 allow pressurized gas supplied to the chamber $C_1$ in each of the sensors 14, 16 to issue toward the passing web W when present to form relatively narrow first and second gas bearings 22, 24 (see FIG. 1b). As should be appreciated, the gas bearings 22, 24 create a repelling force against the faces 14a, 16a of the sensors 14, 16 that prevents the faces 14a, 16a from contacting the passing web W. Of course, since gas bearings 22, 24 are employed, only negligible friction or resistance is created on or against the passing web W.

Each of the first and second sensors 14, 16 also carries at least one magnet 26. It is currently preferred to make each magnet 26 a rare earth magnet recessed in the corresponding substantially flat face 14a, 16a of each sensor 14, 16 (see FIG. 1b). Recessing the magnets 26 advantageously reduces the effects of the highly non-linear force created when a very small or no gap is present between the opposing first and second sensors 14, 16. In the embodiment of FIGS. 1a and 1b, the opposing magnets 26 are polarized to attract each other (that is, the corresponding ends of the magnets 26 have opposite polarities) and are positioned in alignment along a vertical center axis of magnetism such that both attractive and aligning forces are created therebetween. Thus, when the sensors 14, 16 are brought into close proximity to each other and adjacent to the corresponding side of the web W, a magnetic coupling is formed between the magnets 26. This magnetic coupling serves to not only draw the sensors 14, 16 toward one another and the passing web W, but the attractive force also causes the sensors to substantially align with one another in the horizontal plane due to the negligible friction of the gas bearings.

Figure 1C:
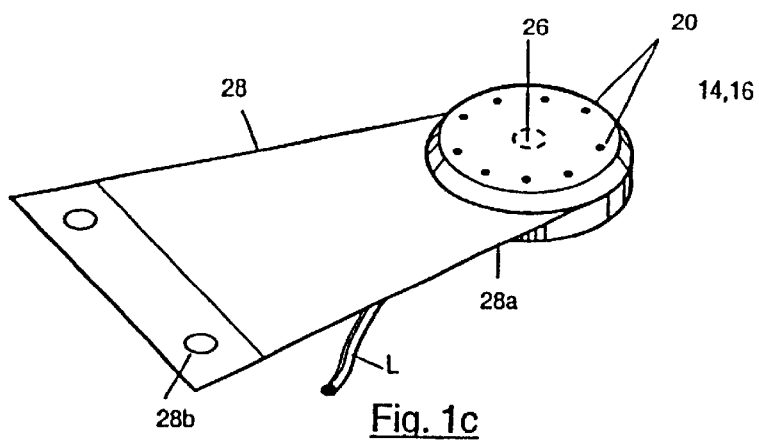
FIG. 1c is a perspective view of one sensor used in the embodiment of FIG. 1a and the corresponding mount that allows it to move in the vertical plane and to tilt.
Figure 2A:
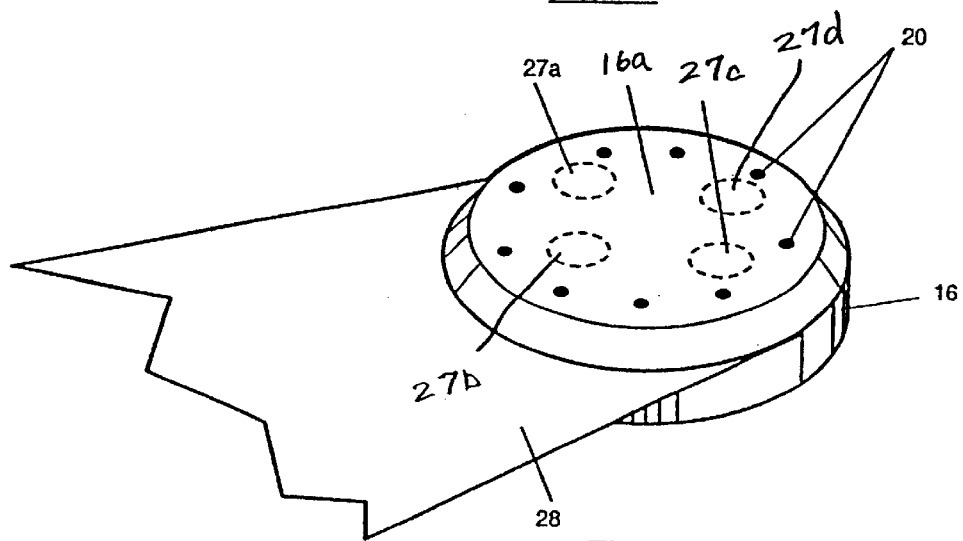
FIG. 2a is an enlarged perspective view of an alternate embodiment of the sensor of FIG. 1a wherein the magnet is comprised of a plurality of magnets, and each one of these magnets are oriented similar to the arrangement in FIGS. 1a–1c.
Figure 2B:
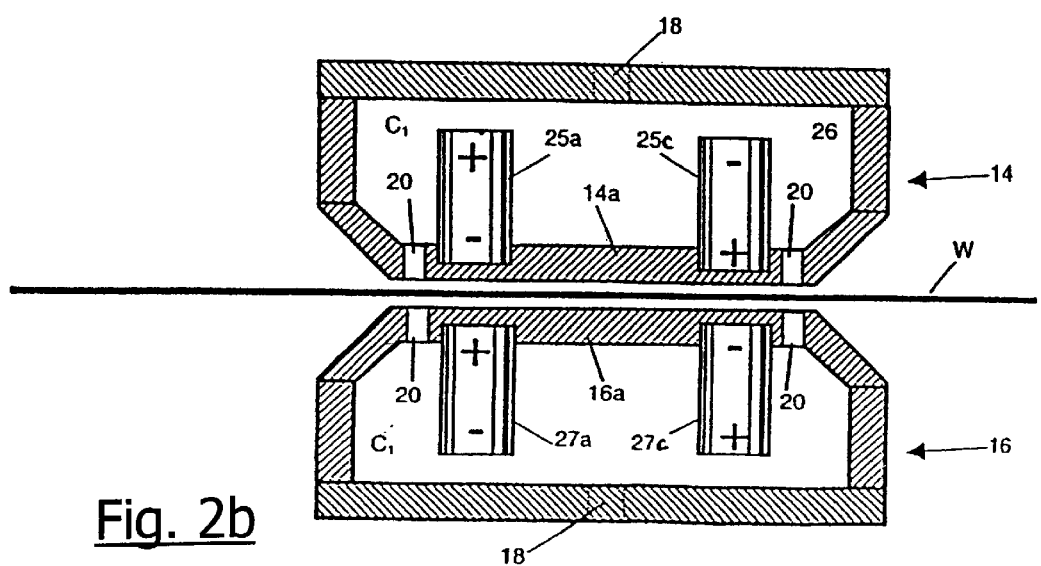
Figure 2C:
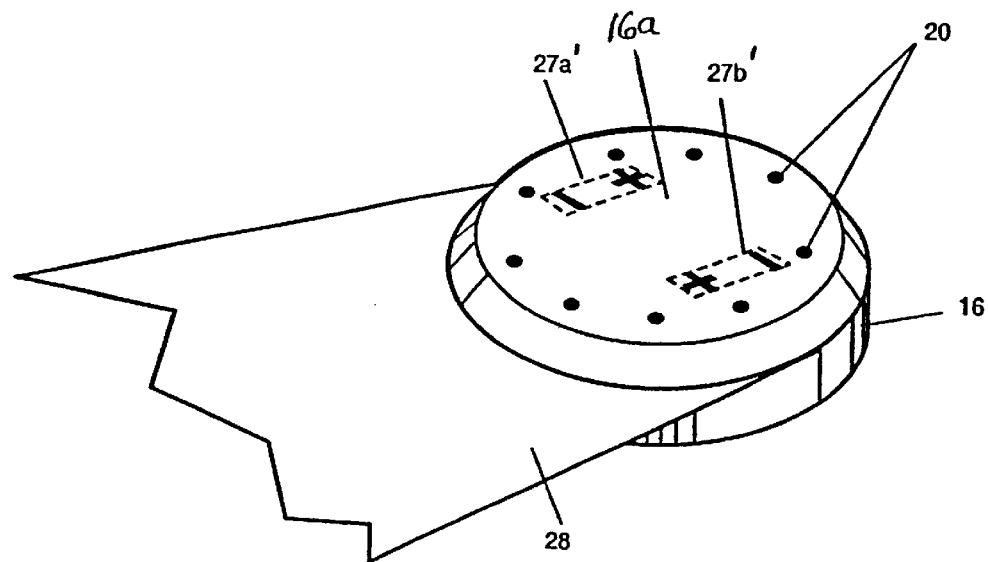
FIG. 2c is an enlarged perspective view of yet another alternate embodiment of the sensor of FIG. 1a wherein the magnet is comprised of a plurality of magnets oriented with their magnetic axes parallel to the face of the sensor.
Figure 2D:
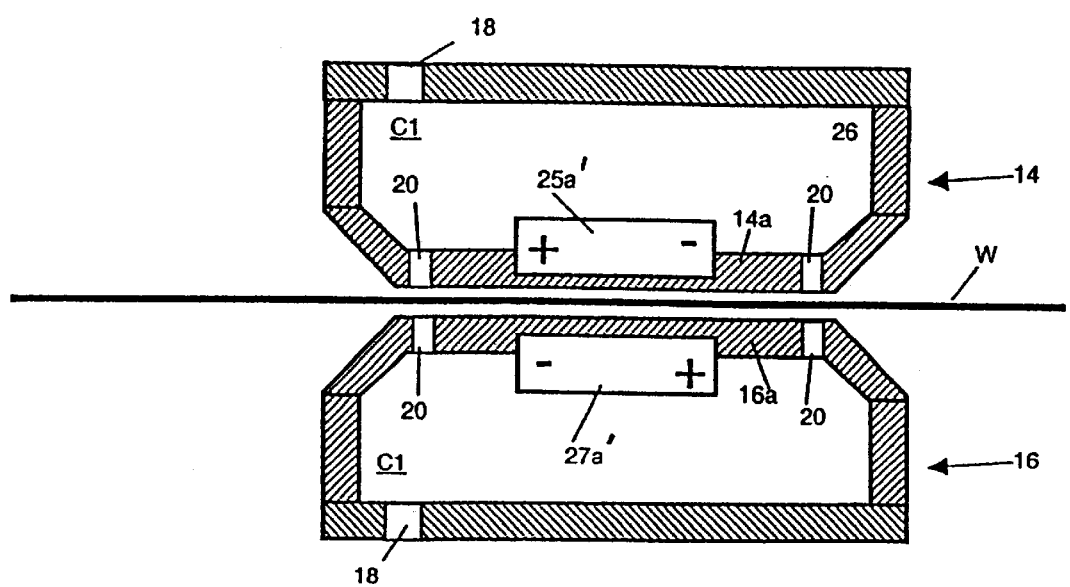
FIG. 2d is a partially sectioned schematic side view of the opposing pair of sensors of the alternate embodiment shown in FIG. 2c.

Although a single magnet 26 is illustrated for each sensor 14, 16 in FIGS. 1a, 1b, and 1c, it should be appreciated that other magnet arrangements are possible. For example, instead of placing a single magnet 26 in the center of each of the sensors 14, 16, one or more pairs of magnets may be provided and spaced symmetrically from the center of the sensors 14, 16. An example illustrating two pairs of magnets 25a–25d paired respectively with 27a –27d is illustrated in FIGS. 2a and 2b. By symmetrically spacing one or more pairs of attracting magnets, space is created within the chambers $C_1$ of the sensors 14, 16 for receiving instrumentation placed at or near the center of the sensors 14, 16. Flat magnets polarized parallel to the sensor flat faces 14a, 16a may also be employed to improve magnetic efficiency and to increase the overall space available in the chambers $C_1$ in the first and second sensors 14, 16 for instrumentation or the like. While one or more pairs of flat magnets may be used in the present invention, two pairs of flat magnets 25a', 27a'; 25b', 27b' are illustrated in FIGS. 2c and 2d. Other magnet arrangements will be suggested to those of skill in the art from the disclosure of the present application. The magnets can consist of permanent magnets or electromagnets. Permanent super magnets made from rare earth elements or similar compounds are advantageous in order to provide a high force to weight ratio of the magnets and to enable small dimensions.

In operation, the repelling force resulting from the gas bearings 22, 24 formed by the pressurized gas issuing from the outlets 20 counterbalances the attractive force created by the magnets 25–27 in each of the first and second sensors 14, 16 so that the sensors 14, 16 are kept from contacting the respective side of the passing web W. The system is controlled so that the resultant net force generated by the attracting force of the magnets 26 and the repelling force created by the gas bearings 22, 24 keeps the sensors 14, 16 substantially evenly spaced from the web W as it passes along the feed path. This even spacing assists in ensuring that accurate sensing and measuring of the desired properties or characteristics of the web W is achieved. Of course, the gaps between the faces 14a, 16a of the sensors 14, 16 and the corresponding sides of the web W can be adjusted by increasing or decreasing the attractive force created by the magnets 26 or the repelling force created by the gas bearings 22, 24, as necessary or desired for a particular type of sensor.

Often, the pass line of the web W changes rapidly and unpredictably as the result of events occurring upstream or downstream from the location where the sensors 14, 16 are positioned, or because of variations in the thickness of the web W. As should be appreciated, since the gas bearings 22, 24 are formed between the opposite surfaces of the web W, the sensors 14, 16 respond to even small changes in the pass line. In other words, when the position of the web W in the vertical plane changes as the feed path varies, each sensor 14 or 16 automatically moves or tilts accordingly and in unison as a result of the bearing action provided by the gas bearing 22 or 24. At the same time, the magnetic coupling between the magnets 26 keeps the sensors 14, 16 substantially evenly spaced from the web W, as well as aligned in the horizontal plane in cases where the sensor mounts permit horizontal movement (see below).

To allow the sensors 14, 16 to react to changes in the vertical position of the web W, including "curling" on the lateral side edges or "tilting" along the sides or midsection, at least one flexible mount 28 is provided. As illustrated schematically in FIG. 1, and perhaps best shown in the perspective view of FIG. 1c, the mount 28 may be a relatively thin sheet of a resilient, polymeric material, such as Kevlar® fabric. The mount 28 has a first end 28a that is secured to the sensor 14 or 16 and a second end 28b for attachment to support structure S, such as by using conventional fasteners (not shown). As a result of the resiliency of the material forming the mount 28, the sensors 14, 16 are capable of moving in the vertical plane in response to similar changes in the pass line of the web W. The movement of the sensors 14, 16 can include tilting in the cross-machine direction as necessary as the mount 28 can twist to accommodate such tilting movement.

Separate mounts 28 are provided for carrying each of the first and second sensors 14, 16.

These mounts may be the same as described above or, as shown schematically in FIG. 1, one or both of the mounts may include a gimbal 29 or other mechanism that permits movement of the corresponding sensor in the horizontal plane as well as in the vertical plane. Also, it is within the broadest aspects of the invention of the present application to provide a stationary or fixed mount for one of the sensors 14 or 16 in combination with a flexible mount 28 of the type shown and described or otherwise for the opposite sensor for applications where the changes in the vertical position or pass line of the web W are small or substantially non-existent.

As briefly mentioned above, instead of providing a single magnet 26 in each of the first and second sensors 14, 16, a plurality of magnets may be provided in each of the sensors 14, 16. An example of one possible arrangement of magnets is shown in FIGS. 2a and 2b. More specifically, the magnet 26 of the first sensor 14 may be supplemented or replaced by a first plurality of magnets 25a . . . 25n (25a–25d illustrated) in the first sensor 14 that align with and correspond to a second plurality of magnets 27a . . . 27n (27a–27d illustrated) in the opposing second sensor 16. The magnets are polarized so as to attract each other. As a result of this polarization, the magnets 25a . . . 25n, 27a . . . 27n attract one another to provide or assist in providing the desired net force to keep the sensors 14, 16 appropriately spaced from each other. The plurality of magnets 25a . . . 25n; 27a . . . 27n in each first and second sensor 14, 16 are preferably arranged in a symmetrical pattern to create a magnetic force that is balanced around the sensor center axis (see the sensor 16 and magnets 27a . . . 27d in FIG. 2a).

The magnetic orientation axes of the magnets 25a . . . 25n and 27a . . . 27n in the first and second sensors 14, 16 does not need to be perpendicular to the faces 14a, 16a of the sensors 14, 16 facing the web W to provide a suitable attractive force between the sensors 14, 16. One arrangement utilizing two pairs of magnets magnetized in the plane of the flat sensor area consists of magnet bars 25a'(25b', not shown) in one sensor head 14, and magnet bars 27a', 27b' in the opposing sensor head 16, as shown in FIGS. 2c and 2d. The magnetic poles are reversed in the opposing magnets of the two sensor heads 14, 16 in order to provide an attractive force. The magnet bars 25a', 25b', 27a', 27b' offers the advantage of compact size. Further, magnetic efficiency is improved since stray magnetic fields are reduced due to the magnets 25a', 25b' and 27a', 27b' facing the opposing magnet with both poles.

To facilitate machine start-up and off-web access to the sensors 14, 16, a second embodiment of the sensor system 10 includes an actuator/retractor 30 for one or both of the sensors 14, 16. As the name suggests, the actuator/retractor 30 actuates one or both of the sensors 14, 16 by moving the sensor(s) toward the web W or pass line when sensing is to be performed and by retracting the sensor(s) away from the web or pass line otherwise. In this way, contact between the sensors 14, 16 is advantageously avoided, as is the concomitant damage that may result from such contact.

Figure 3:
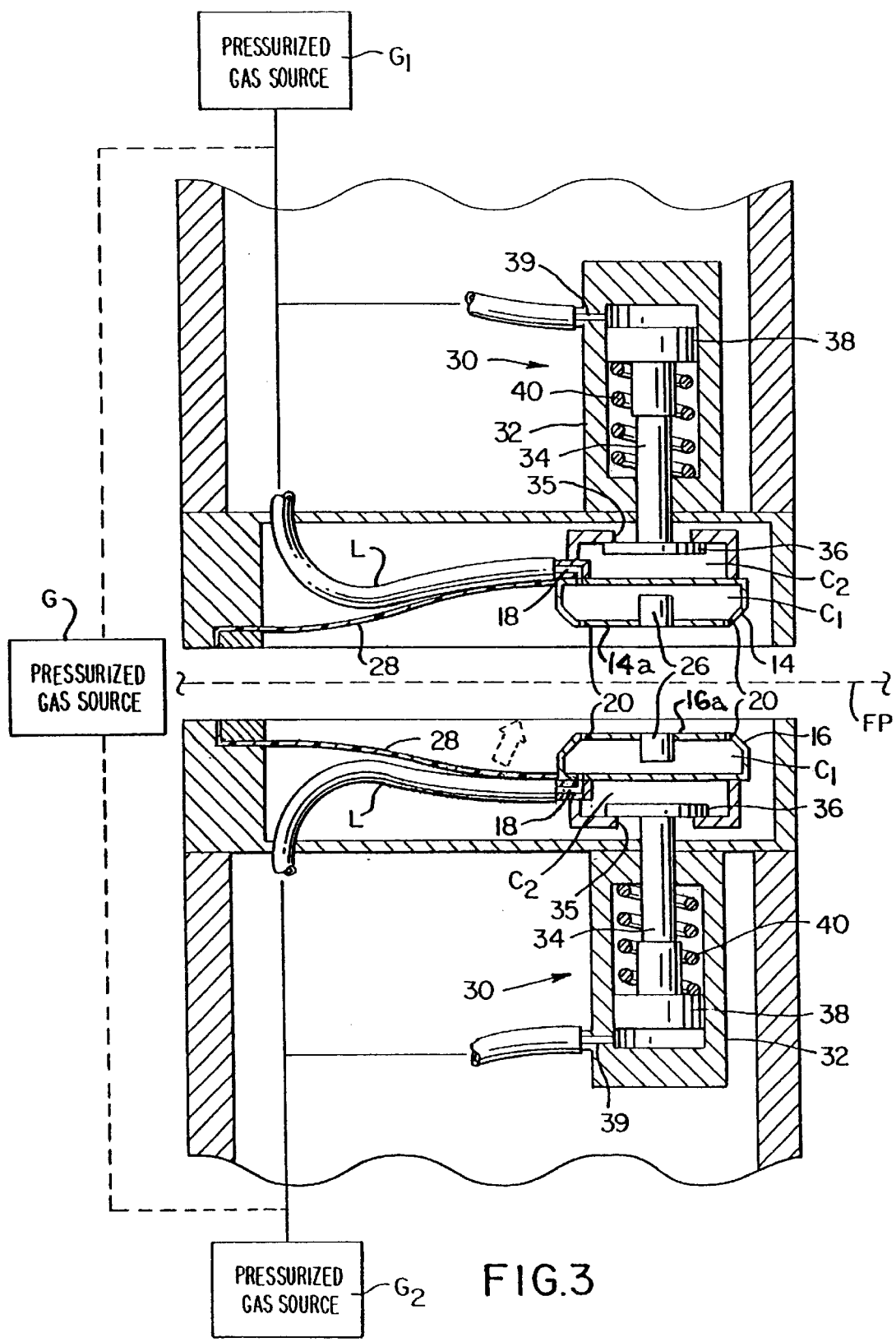
FIG. 3 is a partially sectioned schematic side view of another embodiment of the sensing system of the present invention, including actuators/retractors for selectively moving the sensors away from the web and each other.

In one embodiment, as illustrated schematically in FIG. 3, both of the sensors 14, 16 are provided with an actuator/retractor 30, sometimes also known in the art as a "liftoff" mechanism, although it is within the broadest aspects of the invention of the present application to provide an actuator/retractor 30 for only one of the sensors. Each actuator/retractor 30 includes a pressure-activated cylinder 32 housing a plunger 34. The plunger 34 has a first oversized head 36 for engaging the corresponding sensor 14 or 16 and a second oversized head 38 positioned in the cylinder 32 to engage a biasing means carried in the cylinder 32, such as a helical compression spring 40. The spring force constant of each spring 40 is greater than the attractive force between the magnets 26 at zero gap of the sensors 14, 16. Each cylinder 32 also includes an inlet 39 for receiving a pressurized gas, such as air. The pressurized gas acts against the second head 38 to actuate the corresponding plunger 34 and overcome the biasing force supplied by the associated spring 40. Separate gas sources $G_1$, $G_2$ may be used to supply the gas to each cylinder 32, or as shown in FIG. 3, a common gas source G may be provided for both of the cylinders 32 as well as for supplying the gas forming the gas bearings 22, 24, see below. Instead of a gas, it should be appreciated that the closed nature of the cylinders 32a, 32b also permits pressurized liquids to be used as well.

When each of the cylinders 32 is pressurized, as shown in FIG. 4, the corresponding plunger 34 engages and moves the sensor 14 or 16 associated therewith toward the feed path, the web W, and of course the opposite sensor (see action arrows D). Thus, when the web of paper W or other material is to be sensed, the cylinder 32 of each actuator/retractor 30 is pressurized to actuate the sensors 14, 16. Pressurized gas is supplied to the first and second sensor 14, 16 to create the gas bearings 22, 24 as the magnetic coupling increases with reduction of the gap between the sensors 14, 16. The sensing function is then activated in accordance with the sensing equipment included with the sensors 14, 16.

When the sensors 14, 16 are to be retracted or "lifted-off" the web W, the cylinders 32 are de-pressurized. Upon de-pressurization of the cylinders 32, the springs 40 bias the corresponding plungers 34 away from the web W. As a result of this biasing force, the sensors 14, 16 are retracted from the web W and away from each other such that the magnetic coupling is greatly reduced.

In the illustrated embodiment of the actuators/retractors, as shown in FIGS. 3 and 4, each sensor 14, 16 is carried on the first head 36 of the corresponding plunger 34 by a detachable mounting. The detachable mounting allows the sensors 14, 16 to "float" in at least to the vertical plane, and to some extent in the horizontal plane depending on the type of mount that is used to support the sensors 14, 16, such as the mount 28. More specifically, the oversized head 36 of the plunger 34 extends through an aperture 35 in each sensor 14, 16 which is smaller than the head 36. As a result of this arrangement, the head 36 is captured in a cylindrical second chamber $C_2$ defined in the sensors 14, 16 adjacent to the first chamber $C_1$ (see FIGS. 3 and 4).

In the retracted position, as shown in FIG. 3, the movement of the plungers 34 away from the web W as a result of the biasing force supplied by the springs 40 also moves the sensors 14, 16 away from the web W. However, when the cylinder 32 is pressurized, as shown in FIG. 4 and indicated by vertical action arrows D, the plunger 34 moves toward the web W. In the case of the sensor 14, this motion allows it to move toward one side of the web W, while the sensor 16 is engaged by the plunger head 36 and moved against gravity toward the opposite side of the web W. The pressurized gas is supplied to the sensors 14, 16 to create the repelling force resulting from the gas bearings 22, 24 to thereby not only prevent the sensors 14, 16 from contacting the web W, but also to move them out of engagement with the head 36 of each plunger 34 (see action arrows E). As a result, small gaps F are created between the plunger heads 36 and the sensors 14, 16, which thus "float" above the web W according to the net force resulting from the simultaneous attractive magnetic forces and the repelling bearing forces.

Depending on the relative size of the apertures 35, the sensors 14, 16 may also move slightly from front-to-back and side-to-side in the horizontal plane. The mounts 28 resist this movement and keep the sensors 14, 16 in the illustrated embodiment generally aligned over the same area of the passing web W at all times. As should be appreciated, one of the sensors may not need a mount since the magnetic coupling automatically keeps it aligned with the opposite sensor in the horizontal plane.

In the illustrated embodiment, each pneumatic cylinder 32 is in communication with and activated by a single source of pressurized gas G that also supplies the gas used to form the gas bearings 22, 24 (see the dashed line in FIG. 3 connecting the partially cutaway supply lines with the gas source G). This arrangement is particularly advantageous, since the first and second sensors 14, 16 are automatically retracted upon a loss of pressure in the pressurized gas.

Figure 5A:
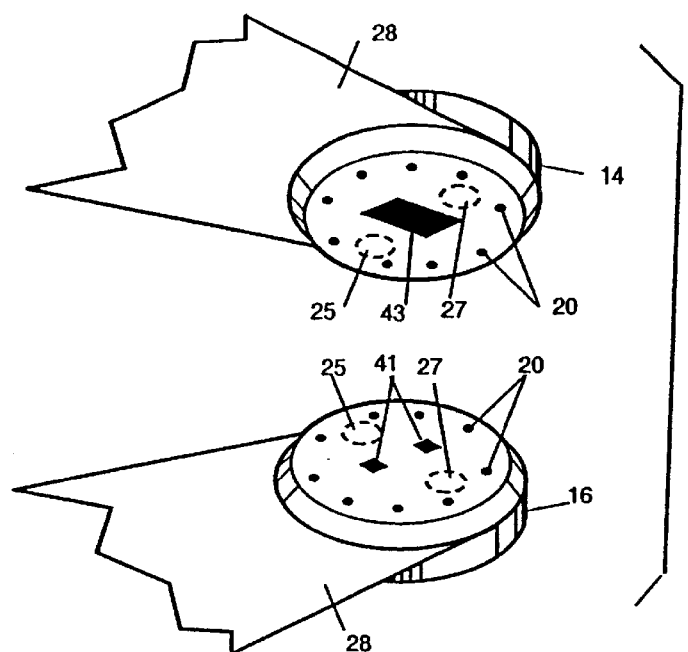
FIG. 5a is a perspective view of a set of opposing sensors similar to those of FIG. 2a but including magnetic distance measuring devices in the two sensors in order to measure the sheet thickness.
Figure 5B:
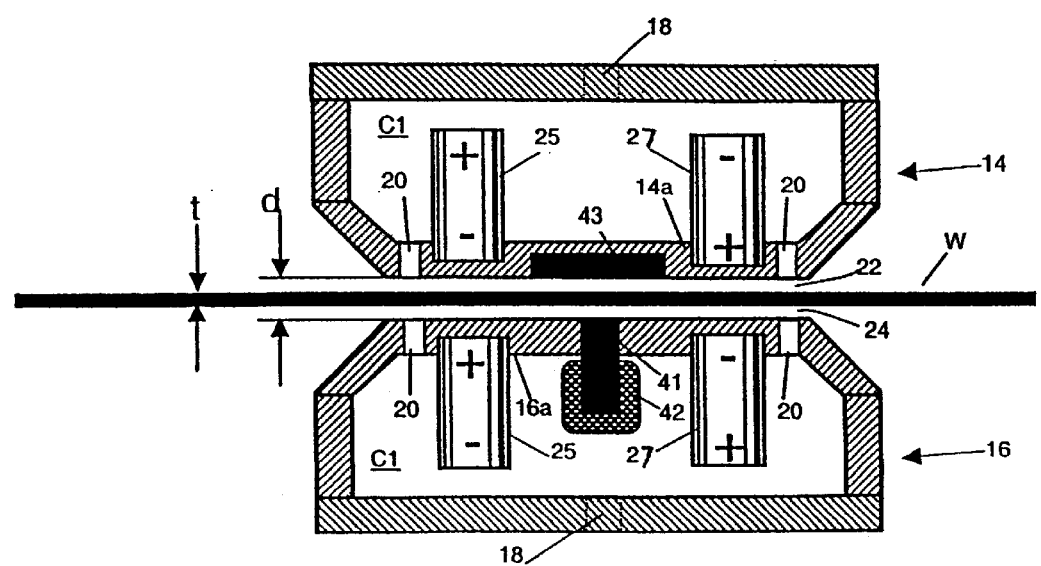

In order to provide a non-contacting measurement of web material properties, various sensing elements are included inside the chambers $C_1$ of the first and second sensors 14, 16. FIGS. 5a and 5b show an embodiment that provides a non-contacting web thickness measurement. FIG. 5a is a perspective view and FIG. 5b is a partially sectioned frontal view of the first and second sensors 14, 16 with the addition of magnetic sensing elements comprising a ferrite C-core 41 and an inductor coil 42 in the second sensor 16, and a ferrite target 43 in the opposing first sensor 14. These sensing elements and associated methods for thickness measurement are known from prior art, for example by U.S. Pat. No. 5,479,720. The sheet thickness t can be calculated from the distance d between the sensors 14, 16 provided that the height of gas bearings 22, 24 remain constant for a given web thickness. The embodiment shown in FIGS. 5a and 5b can be utilized for a simple and low cost non-contacting thickness measurement system, with acceptable accuracy mainly for products that are considerably thicker than the gas bearing heights, for example cardboard.

Figure 6A:
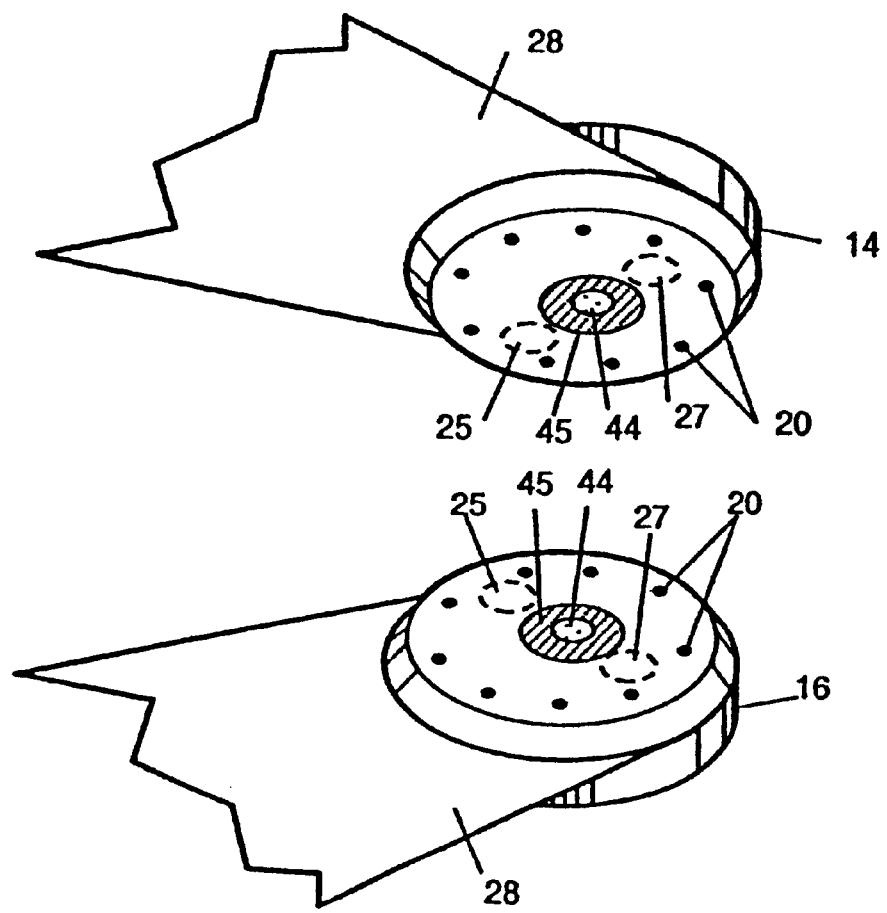
FIG. 6a is a perspective view of a set of opposing sensors similar to those of FIG. 2a but including a magnetic distance measuring system and an optical system for measuring the height of the gas bearings in the two sensors in order to more accurately measure the sheet thickness.

In order to provide thickness measurement with improved accuracy making the measurement system acceptable for use in producing a large variety of web materials including printing paper and tissue products, additional refinements of the invention will now be described. FIG. 6a shows a perspective view and FIG. 6b shows a cross section of the sensors 14, 16 of FIG. 2 with added magnetic sensing devices as well as supplemental gas bearing height sensing elements for non-contacting thickness measurement of the sheet W.

The magnetic sensing elements may comprise a first inductor coil 46 in the sensor 14 and a second inductor coil 47 in the opposing sensor 16 and with wires 48 connected to suitable electronics to measure the gap size d by means of magnetic induction coupling. This principle is well known from prior art. However, due to the self-centering properties of the sensors 14, 16 by the magnet pairs 25, 27 and the low friction gas bearings 22, 24, the induction coils 46, 47 in the invention will always remain coaxially aligned to simplify the inductor coil design and enhance measurement accuracy.

Figure 6B:
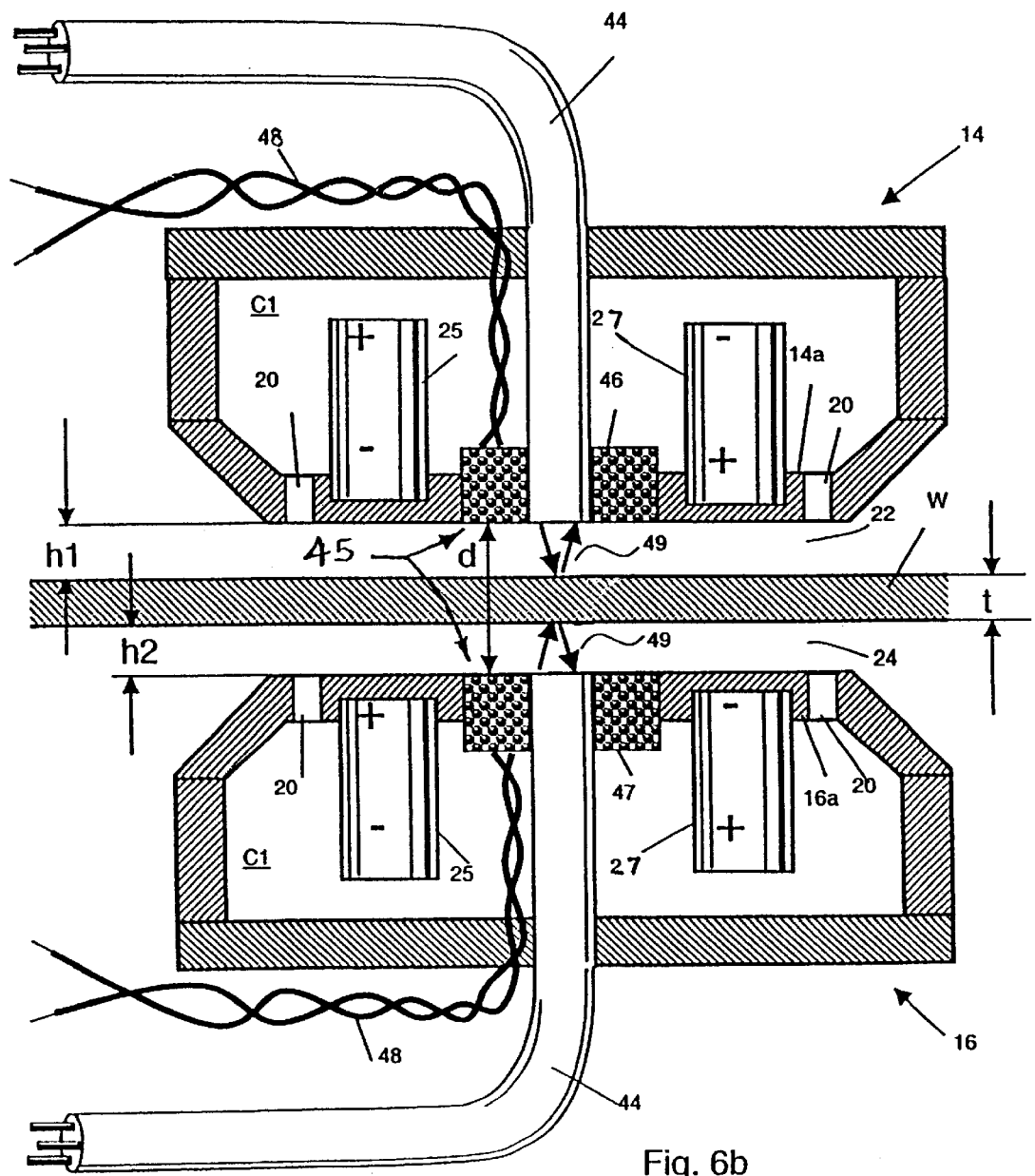

The supplemental sensing elements 44, 45 in FIGS. 6a and 6b are included in order to measure the height $h_1$ of gas bearing 22 and the height $h_2$ of gas bearing 24, in addition to the magnetic measurement of the total gap size d. The sheet thickness t is calculated by the well-known expression:

$$t=d-(h_1+h_2)$$

The distance sensing elements 44, 45 can be mounted inside or outside of the induction coils 46, 47 and may include different known sensors including fiber optics displacement sensors, laser triangulators and ultrasonic devices, signals relating to which are illustrated by arrows 49. However, the invention achieves a closer and controlled proximity of the sensors 14, 16 to the process due to the gas bearings 22, 24 riding on the web W compared to prior art arrangements that use a wide, free sensor gap. This enables improved measurement accuracy of the supplemental sensing devices 44, 45 to determine the distance to the sheet surface.

Figure 7A:
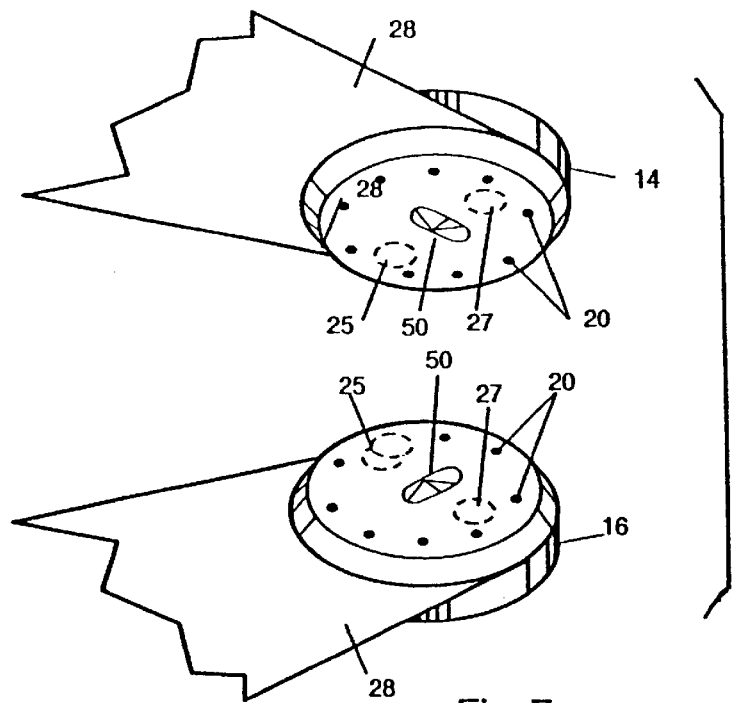
FIG. 7a is a perspective view of a set of opposing sensors similar to those of FIG. 2a but including an optical measurement system in each head to measure gloss of the sheet surfaces.
Figure 7B:
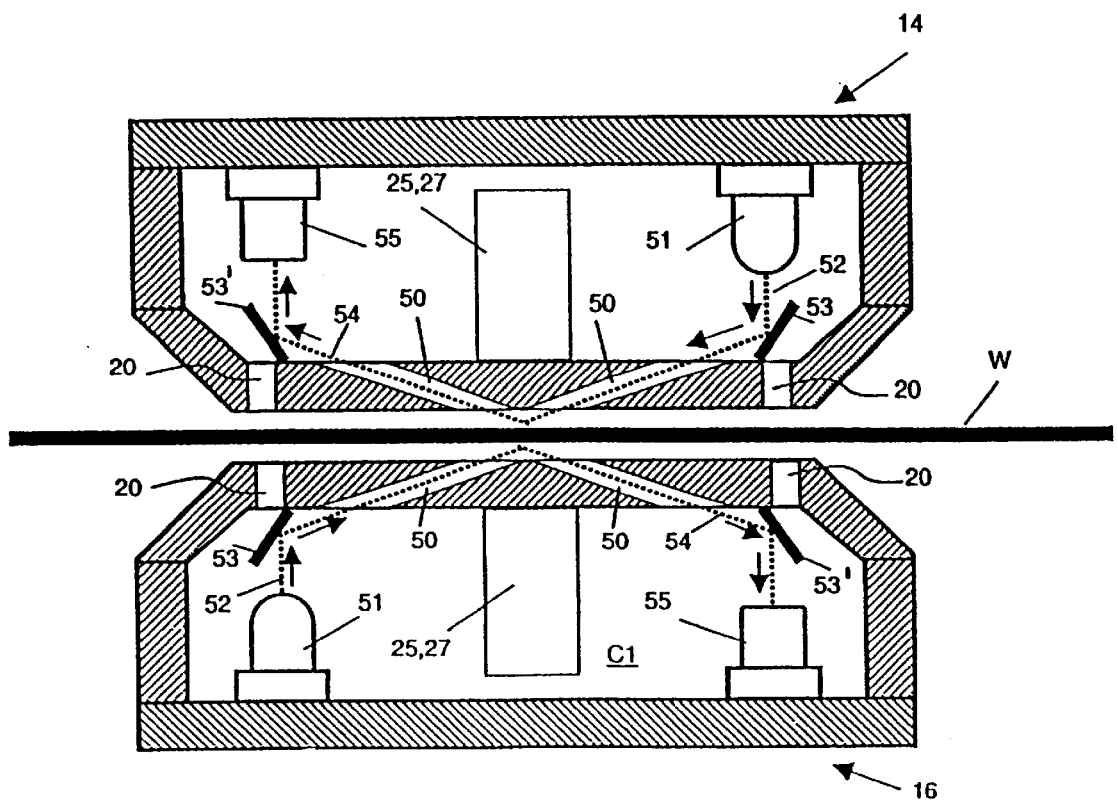

In another embodiment of the invention, improved optical measurement of other sheet properties, for instance gloss or smoothness, is accomplished by embedding appropriate devices in the sensors 14, 16. FIGS. 7a and 7b, respectively, show a perspective view and a schematic cross section of the sensors 14, 16 of FIG. 2 adapted to measure gloss or smoothness on both sides of the web W. Angularly oriented apertures 50 are formed in the sensors 14, 16 to permit measurement of gloss or smoothness of each side of the web W by optical systems included in the sensors 14, 16. The optical systems each comprise a commercially available light source 51 and light detector 55, or may optionally use remote sensing via fiber optics in a manner similar to the supplemental sensing elements 44, 45 of FIGS. 6a and 6b. Light 52 from the light source 51 is directed toward the web W by a first reflective surface 53. Light 54 reflected from the web W is directed toward the detector 55 by a second reflective surface 53' so that the reflected light 54 is received by the detector 55. The controlled and small gap between each of the sensors 14, 16 and the opposite surfaces of the web W, together with the assured parallelism between the sensors 14, 16 and the web W enable the use of miniaturized and narrowly focused optics, due to dimensional scaling rules, to provide improved measurement of gloss and/or smoothness.

A method of sensing or measuring at least one property or characteristic of a web of material moving along a feed path is also disclosed. The method comprises positioning a first sensor 14 on one side of a web W of material moving along a feed path, while a second sensor 16 is positioned in an opposing relationship. The two opposing sensors 14, 16 are then drawn together toward the web W of material by polarized magnets carried by each of the sensors 14, 16 as described above. The first and second sensors 14, 16 are also repelled from one another by a repelling force created by gas bearings 22, 24 formed between the sensors 14, 16 and the adjacent surfaces of the web W. The magnetizing force and repelling force are controlled to maintain the first and second sensors 14, 16 evenly spaced from the passing web W.

Preferably, the first and second sensors 14, 16 have a substantially flat surface 14a, 16a facing the feed path, and the at least one magnet 26 of the first sensor 14 is recessed below the substantially flat surface 14a thereof, while the at least one magnet 26 of the second sensor 16 is recessed below the substantially flat surface 16a of the second sensor 16.

The foregoing description of the invention of the present application has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A non-contact system for sensing or measuring a property or characteristic of a web of material moving along a feed path, said system comprising:
    a first sensor positioned adjacent a first side of said feed path and including a passage receiving pressurized gas and directing said gas toward said web when in said feed path;
    a second sensor positioned adjacent a second side of said feed path and including a passage for receiving pressurized gas and directing said gas toward said web when in said feed path, said first and second sensors being positioned opposite one another across said feed path;
    at least one magnet mounted in said first sensor; and
    at least one magnet mounted in said second sensor, said at least one magnet of said first sensor being aligned with and attracted to said at least one magnet of said second sensor by magnetic coupling to urge said sensors toward said web and one another with said gas directed toward said web from said first and second sensors forming gas bearings to simultaneously urge said sensors away from said web, a net force generated by said magnets and said gas bearings keeping said sensors substantially evenly spaced from said web passing along said feed path to ensure accurate sensing and measuring of said web.

2. A non-contact sensing or measuring system as claimed in claim 1 wherein sensing devices for measuring thickness of said web are included in said first and second sensors.

3. A non-contact sensing or measuring system as claimed in claim 1 wherein sensing devices for measuring glossiness of said web are included in said first and second sensors.

4. A non-contact sensing or measuring system as claimed in claim 1 wherein sensing devices for measuring smoothness of said web are included in said first and second sensors.

5. A non-contact sensing or measuring system as claimed in claim 1 further comprising:
    a first flexible mount for said first sensor; and
    a second flexible mount for said second sensor, said first and second flexible mounts permitting movement of said sensors relative to said feed path so that said first and second sensors remain substantially evenly spaced from the passing web of material.

6. A non-contact sensing or measuring system as claimed in claim 5 wherein at least one of said first and second flexible mounts also prevents movement of an associated sensor in the horizontal plane, said associated sensor thereby preventing movement in the horizontal plane between said first and second sensors by virtue of said magnetic coupling.

7. A non-contact sensing or measuring system as claimed in claim 1 wherein:
    said at least one magnet of said first sensor comprises a first plurality of magnets; and
    said at least one magnet of said second sensor comprises a second plurality of magnets, said first plurality of magnets being aligned with and corresponding to said second plurality of magnets.

8. A non-contact sensing or measuring system as claimed in claim 7 wherein said magnets are symmetrically arranged about a center of each sensor.

9. A non-contact sensing or measuring system as claimed in claim 1 further comprising an actuator associated with at least one of said first and second sensors, said actuator urging said associated sensor toward said feed path and the opposite sensor, and retracting said associated sensor away from said feed path.

10. A non-contact sensing or measuring system as claimed in claim 1 further comprising first and second actuators associated with said first and second sensors, respectively, said first and second actuators urging said first and second sensors toward one another, and retracting said first and second sensors away from one another.

11. A non-contact sensing or measuring system as claimed in claim 10 wherein said first and second actuators each comprise a pneumatic cylinder including a plunger having a first head for engaging its corresponding sensor, each of said cylinders being pressurized so that the corresponding plunger engages and moves the sensor associated therewith toward the feed path and the opposite sensor.

12. A non-contact sensing or measuring system as claimed in claim 11 wherein each said plunger further includes a second head disposed in said pneumatic cylinder for engaging a spring held therein, upon de-pressurizing said pneumatic cylinders said springs bias said corresponding plungers to retract said sensors.

13. A non-contact sensing or measuring system as claimed in claim 11 wherein each said sensor floats on the first head of said corresponding plunger upon actuation thereof as a result of the net force created by the combination of said magnetic coupling and said gas bearings and at least one of said sensors is supported by a flexible mounting that permits movement of said sensors.

14. A non-contact sensing or measuring system as claimed in claim 11 wherein each said pneumatic cylinder is in communication with and activated by said pressurized gas forming said gas bearings so that said first and second sensors are automatically retracted upon a loss of pressure of said pressurized gas.

15. A non-contact system for sensing or measuring a property or characteristic of a web of material moving along a feed path, said system comprising:

first and second sensors positioned on opposite sides of said feed path, each of said first and second sensors including at least one magnet, a passage for receiving pressurized gas and at least one outlet for directing pressurized gas toward said feed path to create first and second gas bearings for the web of material when present, wherein said at least one magnet of said first sensor is aligned with and attracted to said at least one magnet of said second sensor by magnetic coupling that aligns and urges said first and second sensors toward one another and said web, said gas directed from each of said first and second sensors to form said first and second gas bearings simultaneously urging said sensors away from said web and one another so that the net force keeps said sensors substantially evenly spaced from said web moving along said feed path;

a first retractor for engaging and moving said first sensor away from said second sensor and said feed path; and a second retractor for engaging and moving said second sensor away from said first sensor and said feed path.

16. A non-contact sensing or measuring system as claimed in claim 15 wherein said first and second retractors each comprise a cylinder including a pressure-activated plunger having a first head for engaging said corresponding sensor and a second head disposed in said cylinder for engaging a spring held therein, whereby upon relieving the pressure in each said cylinder, said spring biases said second head of said plunger such that said first head of said plunger engages and moves the corresponding sensor away from said feed path.

17. A non-contact sensing or measuring system as claimed in claim 16 wherein said cylinders of said first and second retractors comprise a pneumatic cylinder.

18. In a system for measuring or sensing a property or characteristic of a web of material moving along a feed path, including first and second opposed sensors positioned adjacent to the feed path, each sensor comprising a sensor head including at least one magnet, a passage for receiving pressurized gas and at least one outlet for issuing said pressurized gas towards a passing web of material to form a gas bearing, and wherein said first and second opposed sensors are simultaneously attracted and aligned by said magnets and repelled by said gas bearings to keep said first and second opposed sensors substantially evenly spaced from said moving web.

19. A method of sensing or measuring a property or characteristic of a web of material moving along a feed path, said method comprising the steps of:

positioning first and second opposed sensors adjacent to and on opposite sides of said feed path, each of said sensors including magnets that magnetically couple to one another to align and draw said sensors toward one another and a web of material passing through said feed path; and pressuring passages in said sensors to form a gas bearing on either side of said web so that net magnetic and bearing forces keep the sensors substantially evenly spaced from the passing web.

20. A method as claimed in claim 19 further comprising the step of retracting said sensors when said web of material is not to be sensed.

21. A method of sensing or measuring a property or characteristic of a web of material moving along a feed path, said method comprising the steps of:

positioning a first sensor on one side of a web of material in said feed path;

positioning a second sensor on a second side of said web of material;

drawing said first and second sensors toward one another and said web of material with a magnetizing force; and repelling said first and second sensors from one another and said web of material with a repelling force, said magnetizing force and said repelling force being controlled to maintain said first and second sensors evenly spaced from said passing web.

22. A method as claimed in claim 21 wherein said step of repelling said first and second sensors from one another and said web comprises the steps of:

forming gas bearings in said first and second sensors; and applying pressurized gas to said gas bearings.

23. A method as claimed in claim 22 wherein said step of drawing said first and second sensors toward one another and said web of material comprises the step of:

mounting at least one magnet on said first sensor; and mounting at least one magnet on said second sensor, said at least one magnet on said first sensor and said at least one magnet on said second sensor being polarized to attract one another.

24. A method as claimed in claim 23 wherein said first and second sensors have a substantially flat surface facing said feed path, said method further comprising the steps of:

recessing said at least one magnet of said first sensor below said substantially flat surface of said first sensor; and recessing said at least one magnet of said second sensor below said substantially flat surface of said second sensor.

* * * * *